United States Patent [19]

Maxwell

[11] Patent Number: 4,588,688

[45] Date of Patent: * May 13, 1986

[54] PROCESS FOR THE PRODUCTION OF MUCONIC ACID

[75] Inventor: Peter C. Maxwell, New Providence, N.J.

[73] Assignee: Celanese Corporation, New York, N.Y.

[*] Notice: The portion of the term of this patent subsequent to Oct. 19, 1999 has been disclaimed.

[21] Appl. No.: 516,231

[22] Filed: Jul. 22, 1983

Related U.S. Application Data

[63] Continuation-in-part of Ser. No. 287,344, Jul. 27, 1981, abandoned.

[51] Int. Cl.$^4$ .................. C12P 7/44; C12N 15/00; C12N 1/16; C12R 1/40
[52] U.S. Cl. .................................... 435/142; 435/253; 435/172.1; 435/877; 935/60; 935/83; 935/82
[58] Field of Search ............ 435/136, 142, 145, 172.1, 435/253, 877, 876

[56] References Cited

U.S. PATENT DOCUMENTS

| | | | |
|---|---|---|---|
| 3,383,289 | 5/1968 | Raymond et al. | 435/142 |
| 4,355,107 | 10/1982 | Maxwell | 435/142 |
| 4,400,468 | 8/1983 | Faber | 435/142 |

FOREIGN PATENT DOCUMENTS 0074169  3/1983  European Pat. Off. ............ 435/142

OTHER PUBLICATIONS

Van der Linden et al., "Microbial Oxidation of Hydrocarbons", Advances in Enzymology 27, pp. 506–516 (1965).
Condon et al., "Cold Sensitive Mutation of *Pseudomonas putida* Affecting Enzyme Synthesis at Low Temperature", Journal of Bacteriology 94(6), pp. 1970–1981 (1967).
Tsuji et al., "Accumulation of Cis, Cis-Muconic Acid from Benzoic Acid by a Mutant Induced from Corynebacterium Glutamicum", Hakko Kogoku Kaishi 55(2), pp. 95–97 (1977) Chem. Abst. 86: 167–646.
Gottschalk, "Bacterial Metabolism", Springer-Verlag NY, pp. 126–131 (1979).
Ornston et al., "Isolation of Spontaneous Mutant Strains of *Pseudomonas putida*", Biochemical and Biophysical Research Communications 36(1), pp. 179–184 (1969).
Worsey et al., "Regulation of the Degradative Pathway Enzymes Coded for by the TOL Plasmid (pWWO) from *Pseudomonas putida* mt-2", Journal of Bacteriology 134(3), pp. 757–764 (1978).
Worsey et al., "Characterization of a Spontaneously Occurring Mutant of the TOL20 Plasmid in *Pseudomonas putida* MT20", Journal of Bacteriology 130(3), pp. 1149–1158 (1977).

*Primary Examiner*—Lionel M. Shapiro
*Assistant Examiner*—John E. Tarcza
*Attorney, Agent, or Firm*—Depaoli & O'Brien

[57] ABSTRACT

This invention provides a process for bioconversion of an organic substrate (e.g., ethylbenzene or catechol) to muconic acid.

This invention further provides a procedure for constructing novel strains of microorganisms (e.g., *Pseudomonas putida* Biotype A) which are capable of converting an organic substrate to muconic acid quantitatively by the ortho (catechol 1,2-oxygenase) pathway.

Muconate lactonizing enzyme is not induced in the microorganisms, thereby permitting the muconic acid to be produced and accumulated in a quantity greater than one gram of muconic acid per liter of growth medium.

1 Claim, No Drawings

PROCESS FOR THE PRODUCTION OF MUCONIC ACID

This patent application is a continuation-in-part of patent application Ser. No. 287,344, filed July 27, 1981 now abandoned.

BACKGROUND OF THE INVENTION

Adipic acid is an important commodity in the chemical industry, particularly for consumption as a comonomer in the synthesis of polymers. Adipic acid can be obtained by oxidation of cyclohexane or cyclohexanol. Another prospective method is by the hydrogenation of muconic acid, which is a diolefinically unsaturated adipic acid derivative:

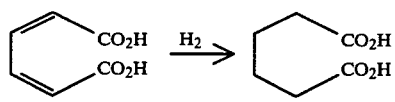

A potentially convenient source of muconic acid is by the microbiological oxidation of various organic substrates. Microbiological oxidation of hydrocarbons is reviewed in Applied Microbiology, 9(5), 383(1961) and in "Advances in Enzymology", 27, 469–546(1965) by Interscience Publishers.

U.S. Pat. No.3,383,289 describes a process for producing a methyl-substituted muconic acid and/or 2,3-dihydroxybenzoic acid which involves subjecting a $C_7$-$C_{10}$ methylbenzene having 1-4 methyl groups and at least two consecutive unsubstituted ring carbon atoms in the presence of a nutrient medium and under fermentation conditions to the action of an orthodihydroxylating and nondecarboxylating strain of Nocardia.

The Journal of Biological Chemistry, 241(16), 3776 (1966) reports the conversion of catechol and protocatechuate to β-ketoadipate by *Pseudomonas putida*. The conversion of catechol proceeds by the ortho pathway via a muconic acid intermediate:

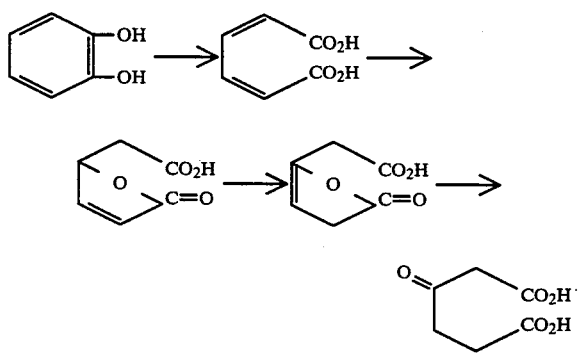

The chemical structures illustrated in the reaction scheme are catechol, muconic acid, muconolactone, β-ketoadipate enollactone and β-ketoadipate, respectively.

In the Journal Of Bacteriology, 134, 756(1978) there is reported a study of the ubiquity of plasmids in coding for toluene and xylene metabolism in soil bacteria. One of the mutant strains of *Pseudomonas putida* isolated had the ability to metabolize toluene via benzyl alcohol, benzaldehyde, benzoic acid and catechol by the ortho pathway through β-ketoadipate to a biomass and carbon dioxide.

The enzymes functioning in the toluene metabolism by the ortho pathway included toluene mono-oxygenase, benzyl alcohol dehydrogenase, benzaldehyde dehydrogenase, benzoate dioxygenase, 1,2-dihydrodihydroxybenzoate dehydrogenase, catechol 1,2-oxygenase and muconate lactonizing enzyme. The subsequently formed β-ketoadipate was further assimilated to biomass and carbon dioxide. The mutant strains that metabolized toluene via the ortho pathway did not accumulate muconic acid, since the said muconic acid metabolite was further transformed in the presence of muconate lactonizing enzyme.

No known naturally occurring microorganisms (e.g., *Pseudomonas putida*) are known that metabolize an organic substrate such as benzene or benzoic acid by the ortho pathway via muconic acid and β-ketoadipate. Wild strains metabolize aromatic hydrocarbon substrates by the meta pathway via 2-hydroxymuconic semialdehyde instead of a muconic acid intermediate. Catechol 2,3-oxygenase is functional rather than catechol 1,2-oxygenase.

Thus, the potential of microbiological oxidation of an organic substrate as an economical source of muconic acid requires the availability of microorganisms which (1) metabolize an organic substrate by means of the ortho pathway via catechol, (2) allow the accumulation of muconic acid without further assimilation, and (3) contain catechol 1,2-oxygenase which is not inhibited by accumulated muconic acid in a bioconversion medium.

Accordingly, it is an object of this invention to provide a process for the efficient conversion of an organic substrate to muconic acid by microbiological oxidation.

It is another object of this invention to provide a process for construction of novel strains of microorganisms which metabolize an organic substrate by the ortho pathway.

It is a further object of this invention to provide a pseudomonad culture which metabolizes catechol to muconic acid quantitatively, with an accumulation of greater than one gram of muconic acid per liter of bioconversion medium.

Other objects and advantages of the present invention shall become apparent from the accompanying description and examples.

DESCRIPTION OF THE INVENTION

One or more objects of the present invention are accomplished by the provision of a process for the production of muconic acid which comprises metabolizing catechol via the ortho pathway to muconic acid in a bioconversion medium, with a microorganism which possesses catechol 1,2-oxygenase with activity that is not inhibited in the presence of any quantity of muconic acid up to about one gram or more per liter of bioconversion medium, and which lacks active muconate lactonizing enzyme.

In another embodiment, this invention provides a process for the production of muconic acid which comprises metabolizing an aromatic substrate by the ortho pathway via catechol to muconic acid in a bioconversion medium, with a microorganism which possesses catechol 1,2-oxygenase with activity that is not inhibited in the presence of any quantity of muconic acid up to about one gram or more per liter of bioconversion medium, and which lacks active muconate lactonizing enzyme.

In a further embodiment, this invention provides a process for the production of muconic acid which comprises metabolizing an aromatic substrate to catechol or a catechol precursor in a bioconversion medium, and further metabolizing the catechol or catechol-precursor to muconic acid with a microorganism which possesses catechol 1,2-oxygenase with activity that is not inhibited in the presence of a low level of muconic acid in the bioconversion medium, and which lacks active catechol 2,3-oxygenase and muconate lactonizing enzyme. A preferred microorganism is one which has been modified to possess catechol 1,2-oxygenase with activity that is not inhibited in the presence of any quantity of muconic acid up to about one gram or more per liter of bioconversion medium.

The rate of organic substrate conversion typically is about or greater than 30 milligrams of muconic acid produced per dry weight gram of cells per hour. The conversion of organic substrate proceeds readily at a dry weight cell concentration of about 50 grams per liter, with a resultant muconic acid production rate of at least about 1.5 grams per liter per hour.

Under optimal conditions, the muconic acid accumulation limit can approach up to about 50 grams of muconic acid per liter of bioconversion medium. The microbiological oxidation process normally is conducted at ambient temperatures up to about 31° C.

The organic substrates which are suitable for bioconversion in accordance with the present invention include aromatic compounds such as benzene, ethylbenzene, styrene, naphthalene, anthracene, phenol, o-cresol, benzyl alcohol, benzaldehyde, benzoic acid, aniline, anthranilic acid, salicylic acid, and the like.

The ortho pathway (also known as the β-ketoadipate pathway or the catechol 1,2-oxygenase pathway) has been studied in *Pseudomonas putida, Acinetobacter calcoaceticus,* and *Alcaligenese eutrophus.* Research effort for the most part has concentrated on the metabolism of benzoate. The organisms are ubiquitous in nature and are easily isolated by enrichment culture on media containing benzoate as the sole source of carbon. The initial reaction in the metabolism of benzoate is transport of the molecule into the cell followed by conversion of benzoate via dihydrodihydroxybenzoate to catechol. The series of enzymes which convert catechol to β-ketoadipate constitute the ortho pathway proper. The first of these enzymes, catechol 1,2-oxygenase, is the enzyme responsible for the conversion of catechol to muconic acid as described above.

A microorganism provided for the practice of a present invention process embodiment has characteristics which are unique for the microbiological conversion of an aromatic substrate and the production and accumulation of muconic acid.

First, the microorganism metabolizes an aromatic substrate by the ortho pathway via catechol cleavage by the action of catechol 1,2-oxygenase. Concomitantly, no active catechol 2,3-oxygenase is induced in the microorganism culture.

Second, the catechol 1,2-oxygenase activity is not repressed or inhibited by the presence of a low level of muconic acid, e.g., a low level of muconic acid up to about one gram/liter in the growth medium. This permits the accumulation of muconic acid at a level which is higher than about one gram/liter.

Third, the ortho pathway series of conversion reactions is blocked subsequent to the formation of the muconic acid from catechol. The microorganism lacks the presence of active muconate lactonizing enzyme. Hence, the muconic acid is able to accumulate as it is produced, i.e., the muconic acid accumulates up to a level of about 50 grams per liter of bioconversion medium. No microorganism reported in the literature is known to exhibit the ability to produce and accumulate muconic acid to these levels from an organic substrate.

Illustrative of suitable microorganisms are constructed strains of pseudomonads each of which has the following characteristics:
  (a) possesses active benzoate dioxygenase and 1,2-dihydrodihydroxybenzoate dehydrogenase and catechol 1,2-oxygenase;
  (b) lacks active catechol 2,3-oxygenase; and
  (c) does not grow on benzoate or halobenzoate;
and the microorganism is capable of metabolizing an aromatic substrate by the ortho pathway via catechol quantitatively to an accumulated quantity of muconic acid greater than about one gram per liter of a bioconversion medium. "Quantitative" refers to a conversion selectivity to muconic acid of at least about 90 percent.

Illustrative of a preferred type of microorganism is a strain of fluorescent Pseudomonad having the following characteristics:
  (a) possesses active benzoate dioxygenase;
  (b) possesses active 1,2-dihydrodihydroxy-benzoate dehydrogenase;
  (c) possesses catechol 1,2-oxygenase with activity that is not inhibited in the presence of any quantity of muconic acid up to about one gram or more per liter of a bioconversion medium;
  (d) lacks active muconate lactonizing enzyme;
  (e) lacks active catechol 2,3-oxygenase enzyme;
  (f) does not grow on benzoate or monohalobenzoate; and
  (g) cells are rod shaped, vigorously motile and polarly flagellated.

A novel strain of *Pseudomonas putida* Biotype A having the above recited characteristics, has been deposited with the American Type Culture Collection and has been designated as ATCC No. 31916.

In a further embodiment, the present invention contemplates a process for the construction of novel microorganism strains which comprises (1) culturing a microorganism species selectively to provide strain A1 which metabolizes a selected organic substrate by the ortho pathway via catechol to muconic acid, and which subsequently metabolizes the resultant muconic acid via β-ketoadipate to biomass and carbon dioxide; (2) continuously and selectively culturing strain A1 for rapid growth on the organic substrate as the sole source of carbon to provide strain A2; (3) culturing strain A2 in selective enrichment cycles in a medium containing benzoate as the sole source of carbon and containing an antibiotic which kills only growing cells; (4) harvesting the strain A2 cells and diluting and culturing the cells in media containing a non-selective carbon source; (5) plating the strain A2 cells on a nutrient medium containing a limiting amount of a non-selective carbon source and excess benzoate; (6) isolating cells from single small colonies, and culturing the cell isolates and selecting a strain A3, wherein strain A3 converts the selected organic substrate to accumulated muconic acid.

The starting microorganism can be any organism capable of growth on the selected organic substrate and possessing a catechol 1,2-oxygenase, e.g., a pseudomonad. A variety of naturally occurring organisms have these traits including some members of the species *Pseudomonas putida, Pseudomonas aeruginosa, Pseudomonas fluorescens;* some members of the genera Azotobacter and Nocardia; and a number of unclassified fungi (both molds and yeasts).

The disclosure of copending patent application Ser. No. 516,088, filed July 22, 1983 is incorporated by reference.

Microorganism Construction Procedure

The first step is to isolate a mutant of an original microbial isolate which grows on a selected organic substrate via the ortho pathway, i.e., the pathway in which muconic acid is an intermediate. The following procedure is described in reference to a catechol-precursor type of organic substrate, e.g., ethylbenzene.

The original isolate is first made constitutive for growth on m-toluic acid. This first strain is then subjected to a cycle designed to eliminate the meta pathway and select for cells which have retained the ability to grow on the selected organic substrate. Cells are first grown from low dilution on benzoic acid. These cells are transferred to medium containing m-toluic acid as the sole source of carbon. After one hour, the antibiotics penicillin and D-cycloserine are added at concentrations of 12 and 0.1/mg/ml and the incubation is continued for four to six hours. After the incubation, the cells are washed and transferred at a 50:1 dilution to a medium containing the selected organic substrate as the sole sources of carbon. Visible growth occurs in approximately thirty-six hours.

When plated on agar containing benzoate a mixture of small and large colonies are formed. Virtually all of the large colonies metabolize the organic substrate via the ortho pathway, thus producing muconic acid as an intermediate. This second strain, characterized by growth on the organic substrate via the ortho pathway, does not possess an active catechol 2,3-oxygenase. Its doubling time on the organic substrate is approximately four hours.

The second strain is then subjected to selection for a rapid growth rate by being continuously cultured on the organic substrate as the sole source of carbon. Once the culture has stabilized at a doubling time of approximately four hours, the dilution rate is increased to require a doubling time of three hours. This process is repeated until the cells are growing with the shortest possible doubling time, e.g., two hours. This third strain differs from its parent at least in having catechol 1,2-oxygenase which is not inhibited by a low level of muconic acid in the bioconversion medium.

The third strain converts the organic substrate to muconic acid but also converts muconic acid to biomass and carbon dioxide. To obtain a strain which accumulates muconic acid, it is necessary to isolate cells lacking a functional muconate lactonizing enzyme. The third strain is grown overnight on the organic substrate. These cells are transferred to media containing benzoic acid as the sole source of carbon. After one hour, penicillin and D-cycloserine are added and the incubation is continued for four to six hours. After the incubation, the cells are harvested, washed and transferred at a 500:1 dilution to medium containing p-hydroxybenzoate as the sole source of carbon. Cells grown overnight on p-hydroxybenzoate are transferred to medium containing benzoate as the sole source of carbon and the enrichment cycle is repeated. After six cycles, the survivors are plated on agar containing 5 mM benzoic acid and 0.5 mM succinic acid. On this medium, cells unable to metabolize benzoate form small colonies.

The single small colonies are picked and cultured, and after induction with the organic substrate, checked for their ability to produce muconate. A strain is selected which exhibits an ability to convert the organic substrate to muconic acid in an efficient manner.

The following examples are further illustrative of the present invention. The components and specific ingredients are presented as being typical, and various modifications can be derived in view of the foregoing disclosure within the scope of the invention.

The basal salts medium employed for all of the series has the following composition (NO medium):
50 mM of $Na_2HPO_4$
100 mM of $KH_2PO_4$
17 mM of $(NH_4)_2SO_4$
1 mM of $MGSO_4$
0.1 mM of $CaCl_2$
0.01 mM of $FeSO_4$ The medium has a pH of 6.2, and the original organism used in the Examples is constructed from a natural isolate.

For cultivation, organic substrate carbon sources such as ethylbenzene are added aseptically prior to inoculation. Incubation conditions are in 250 ml shake flasks. Shaking is in a rotary shaker with temperature controlled at 28° C.

The organic substrate is delivered to the shake flasks either from an ethanol sterilized dialysis bag or from a 5 ml layer of paraffin wax in the bottom of the flask. In the latter case, molten paraffin is pipetted into the flask, the flask is autoclave sterilized, and while still hot, the organic substrate is added and mixed with the paraffin. After solidifying, the sterilized basal salts medium is added aseptically. In the case of the dialysis bags, the dialysis tubing is washed extensively and boiled to remove the glycerol which is incorporated as a plasticizer. Enough glycerol remains to support the growth of the microorganisms to the extent of approximately $6 \times 10^8$ cells per ml. In this system, only growth in excess of $7.5 \times 10^8$ ml is considered significant. The basal salts medium is capable of supporting growth of $3.3 \times 10^9$ cells per ml when there was an unlimited carbon source.

Growth is typically measured by determining the turbidity of the cell suspension in a Klett-Summerson Colorimeter using the #66 red filter. One Klett unit is considered to be equivalent to about $3 \times 10^6$ cells per ml or 17.5 mg wet weight per liter of 3.5 mg dry weight per liter.

Cultures are stored under liquid nitrogen.

EXAMPLE I

This Example illustrates the isolation of ethylbenzene oxidizing microorganisms.

Soil samples are collected from a variety of areas and added to medium plus paraffin containing ethylbenzene. After shaking at 28° C. for 24 hours growth is apparent in the medium. Strains are isolated by streaking on agar plates containing a vial of ethylbenzene in the lid. Colonies appear on the agar after approximately 30 hours. The size of these colonies ranges from 1 to 5 mm. A representative sampling of these colonies is taken and cultures are stored under liquid nitrogen for long-term preservation.

A strain derived from one of the largest colonies is chosen for further work and designated MW 2000. This strain is identified as a *Pseudomonas putida* Biotype A on the basis of the following criteria:

(a) the cells are rod shaped, vigorously motile and polarly flagellated;
(b) cells grow well on benzoate and p-hydroxybenzoate;
(c) cell growth on benzoate induces the synthesis of carboxymuconate lactonizing enzyme and carboxy-muconolactone decarboxylase but not protocatechuate oxygenase, a pattern of regulation characteristic only of the *Pseudomonas putida* Biotype A;
(d) the induced enzymes muconolactone isomerase, carboxy-muconate lactonizing enzyme, and carboxy-muconolactone decarboxylase are immunologically identical with those enzymes synthesized by *Pseudomonas putida* Biotype A, a saprophytic organism extensively studied in the literature.

Ethylbenzene grown MW 2000 consumes oxygen when presented with ethylbenzene, 2-phenylethanol, 2-phenylacetaldehyde, 2-phenylacetic acid or catechol. With catechol the medium turns yellow indicating the production of excess 2-hydroxymuconic semialdehyde.

The presence of the meta pathway is confirmed by demonstration of 2,3-oxygenase activity in cell free extracts.

EXAMPLE II

This Example illustrates a copending patent application Ser. No. 516088 type procedure for constructing a strain of organism which oxidizes ethylbenzene via the ortho (β-ketoadipate) pathway.

A series of mutants which metabolize ethylbenzene through the ortho pathway is constructed by first blocking the meta pathway and then isolating phenotypic revertants which have reacquired the ability to grow on benzoate. Strains possessing a meta pathway block are isolated after penicillin plus D-cycloserine enrichment for organisms which failed to grow on benzoate. A selection of isolates are then spotted onto agar plates and incubated in the presence of ethylbenzene. Most of the isolates revert to growth on ethylbenzene. The plates are sprayed with 10 mM catechol and some of the revertants are found not to produce 2-hydroxymuconic semialdehyde. None of the colorless revertants (MW 2200) are found to possess an active catechol 2,3-oxygenase following induction with ethylbenzene.

It has been shown by Worsey and Williams, J. Bacteriol. 130, 1149 (1977) that growth on benzoate tends to cure a population of its TOL plasmid because the ortho pathway supports a higher growth rate. Since toluate can only be metabolized via the meta pathway, an alternative way to cure a population of its TOL plasmid is to use the penicillin plus D-cycloserine procedure to enrich for cells unable to grow on toluate.

Both these techniques are used in succession followed by counter-selection for growth on ethylbenzene. MW 2200 is first cultured on ethylbenzene. A small portion (0.05 ml) of this culture is transferred to 50 ml of benzoate medium. After growth on benzoate the cells are transferred to toluate and incubated for approximately one hour. Penicillin and D-cycloserine are then added as described above and the incubation is continued for four to six hours. Cells are harvested, washed and transferred to an ethylbenzene containing medium.

After growth on ethylbenzene the cells are plated on benzoate agar and incubated for 48 hours, and a number of large colonies and a few small colonies are formed. After spraying with catechol it is found that all of the small colonies turn yellow (indicating the presence of the meta pathway) but none of the large colonies do. Large colonies are picked and cultured and it is found that, following growth on ethylbenzene, these strains contained no functional 2,3-oxygenase but are fully induced for the 1,2-oxygenase. These strains metabolize ethylbenzene by the ortho pathway. One isolate, designated MW 2210, is selected for further work.

EXAMPLE III

This Example illustrates the construction of a novel *Pseudomonas putida* Biotype A strain.

The strain of Example II is subjected to continuous cultivation with ethylbenzene as the sole source of carbon. Initially a dilution rate of 0.15 hours$^{-1}$ is employed. After the culture has stabilized, the dilution rate is increased successively to 0.25 hour$^{-1}$, 0.34 hour$^{-1}$, and 0.46 hour$^{-1}$. An isolate is made from the cells which dominate the culture at this latter dilution rate. This strain is then used to construct a strain which accumulates muconic acid to greater than one gram per liter.

The above strain is cultured overnight in liquid medium on ethylbenzene as the sole source of carbon, then benzoate is added to a level of 5 mM and the incubation is continued for approximately 1 hour. Penicillin G and D-cycloserine are added at concentrations of 12 and 0.1 mg/ml respectively. The antibiotic incubation is continued for approximately 5 hours. The cells are then harvested by centrifugation and washed twice with sterile de-ionized water. An aliquot of these cells is then transferred to fresh medium containing 0.5 mM p-hydrobenzoate as a sole source of carbon, and the medium is incubated overnight. The procedure is repeated starting with induction with benzoate.

After 6 cycles those cells present in the culture after overnight growth on p-hydroxybenzoate are diluted and plated on an agar medium containing 0.5 mM succinate and 5.0 mM benzoate as sole sources of carbon. After 36 hours incubation the plate shows a mixture of large and small colonies. Cells from a number of small colonies are cultured in liquid medium, induced with ethylbenzene and tested for their ability to accumulate muconic acid. Of the isolates, at least one strain is an accumulator of muconic acid.

EXAMPLE IV

This Example illustrates the bioconversion of ethylbenzene to muconic acid with an accumulation of greater than one gram of muconic acid per liter of conversion medium.

The microorganism employed is a strain of *Pseudomonas putida* Biotype A as described in Example III.

Succinate is used as the source of carbon in the medium containing the Pseduomonas culture. After reaching a stationary phase, ethylbenzene is added to the medium to induce the appropriate enzymes. After about 2.5 hours, the cells are harvested by centrifugation and washed with buffer.

The conversion is performed in 150 mM of sodium potassium phosphate buffer at a pH of 7.5. The cell concentration is adjusted to 50 gm dry weight per liter. Ethylbenzene is added slowly in the vapor phase by bubbling the air or oxygen stream through an ethylbenzene reservoir. The concentration of muconic acid thereby produced is determined spectrophotometrically by the increase in absorbance at 260 nm. The muconic acid concentration increases to above about 15 grams/liter before the bioconversion reaction becomes inhibited.

The identity of the muconic acid product is confirmed by high pressure liquid chromatography, melting point, and nuclear magnetic resonance.

EXAMPLE V

This Example illustrates the bioconversion of catechol to muconic acid, employing ATCC No. 31916 strain of *Pseudomonas putida* Biotype A.

Cells of ATCC No. 31916 strain are inoculated into a Chemap 10 liter fermentor containing NO medium and 20 mM gluconate as a carbon source. The fermentor temperature is controlled at 29° C., the agitation rate is 800 rpm and the air flow rate is 2.8 l/min.

After overnight incubation, the culture turbidity is 226 Klett units (0.79 g/l). At this point, feeds of acetic acid at a rate of 0.198 g/l hr and catechol (from a 1M solution) at a rate of 2.22 mM/hr are begun. The acetic acid is added to ensure adequate carbon and energy for maintenance and enzyme synthesis (the absence of supplemental acetic acid yields substantially the same results). A pH of 6.4 is controlled by automatic addition of 2 N NaOH.

Muconic acid synthesis begins immediately and continues at the same rate as catechol addition. The total quantity of catechol added is 400 mM and the reservoir is depleted in approximately 1023 minutes. The conversion of catechol to muconic acid is quantitative.

What is claimed is:

1. A process for the production of muconic acid which comprises metabolizing catechol via the ortho pathway to muconic acid in a bioconversion medium, with a microorganism which possesses catechol 1,2-oxygenase with activity that is not inhibited in the presence of a low level up to about one gram or more of muconic acid per liter of bioconversion medium, which lacks active muconate lactonizing enzyme and active catechol 2,3-oxygenase, which is capable of metabolizing catechol quantitatively to an accumulated quantity of muconic acid greater than about one gram per liter of the bioconversion medium, and which has the identifying characteristics of *Pseudomonas putida* Biotype A strain ATCC No. 31916.

* * * * *